United States Patent

Seckinger et al.

[11] Patent Number: 5,457,085
[45] Date of Patent: Oct. 10, 1995

[54] OPTICAL ISOMER OF DIMETHENAMID

[75] Inventors: Karl Seckinger, Riegel, Germany; Reynold Chollet, Bottmingen, Switzerland; Stefan Blarer, Basel, Switzerland; Thomas Vettiger, Allschwil, Switzerland

[73] Assignee: Sandoz Ltd., Basel, Switzerland

[21] Appl. No.: 310,198

[22] Filed: Sep. 21, 1994

Related U.S. Application Data

[63] Continuation-in-part of Ser. No. 44,998, Apr. 9, 1993, abandoned, which is a continuation of Ser. No. 976,802, Nov. 16, 1992, abandoned.

[51] Int. Cl.$^6$ .......................... A01N 43/10; C07D 333/36
[52] U.S. Cl. .............. 504/289; 549/68; 549/69; 564/503
[58] Field of Search ............. 549/69, 68; 504/289; 564/503

[56] References Cited

U.S. PATENT DOCUMENTS 5,002,606  3/1991  Moser et al. ............... 71/118

FOREIGN PATENT DOCUMENTS 2114566  8/1983  United Kingdom .

OTHER PUBLICATIONS

Harr et al, Proceedings of an international conference organised by the British Crop Protection Council, Brighton Centre and Brighton Metropole, Brighton, England Nov. 18–21, 1991.

*Primary Examiner*—Richard L. Raymond
*Attorney, Agent, or Firm*—Lynn Marcus-Wyner; Allen E. Norris

[57] ABSTRACT

The invention relates to (1S,aRS)-2-chloro-N-(2,4-dimethyl-3-thienyl)-N-(2-metho1xy-1-methylethyl)acetamide, a novel method of preparation, herbicidal compositions comprising said compound and methods of combatting weeds employing said compound.

8 Claims, No Drawings

OPTICAL ISOMER OF DIMETHENAMID

This application is a continuation-in-part of U.S. application Ser. No. 8/044,998, filed Apr. 9, 1993, now abandoned which is a continuation application of U.S. Ser. No. 07/976,802, filed November 16, 1992, now abandoned.

The invention relates to (1S, aRS)-2-chloro-N-(2,4-dimethyl-3-thienyl)-N-(2-methoxy-1-methylethyl)acetamide.

UK Patent Specification 2,114,566 discloses (1RS, aRS)-2-chloro-N-(2,4 -dimethyl-3-thienyl)-N-(2-methoxy-1-methylethyl)acetamide-also known under the common name dimethenamid-and its use as a herbicide in corn, soybeans, sugarbeet, sunflower and several other crops.

Dimethenamid allows the control of a wide variety of annual grasses including Echinochloa crus-galli, Digitaria spp., Eleusine indica, Panicum spp., Setaria spp. and Alopecurus myosuroides but also several broad leaved weeds including Amaranthus spp., Capsella bursa-pastoris, Chenopodium album, Cammelina spp., Matricaria chamomilla and Mullogo verticiilata.

Dimethenamid consists of 4 stereoisomers due to two chiral elements: the chiral axis (a)-along the bond between the 3-position of the thiophene ring and the N-atom of the amide function-and the asymmetrically substituted carbon atom of the 2-methoxy-1-methylethyl group which is tied to the amide function.

Hitherto it was suggested that Dimethenamid, when employed at rates needed for good weed control (ca. 85% weed control or more) under field conditions, was about as active as the diastereomeric mixture (1S,aRS) at the same rate, indicating that it was not beneficial to eliminate the (1R, aRS) mixture from Dimethenamid.

A suitable application rate for Dimethenamid when used alone is, depending on the conditions such as soil type, in the range of from 0.75 to 1.5 kg/ha, conveniently about 1200 to 1500 g/ha.

It has now been found that (1S,aRS)-2-chloro-N-(2,4-dimethyl-3 -thienyl)-N-(2-methoxy-1-methylethyl)acetamide

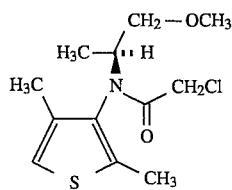

(I)

hereinafter for convenience designated S-Dimethenamid of formula I—is particularly effective against various important weeds. This is i.a. observed after pre-emergence application of Dimethenamid and S-Dimethenamid under field conditions in corn at application rates of 125, 250, 500, 750, 1000, 1500, 2000 and 3000 g/ha of Dimethenamid and of 125, 250, 500, 750, 1000 and 1500 g/ha of S-Dimethenamid (application volume of 660 lt per ha).

The results are in line with i.a. results found after application of the test compounds at application rates corresponding with 6, 19, 56, 168 and 505 g a.i./ha under greenhouse conditions (spray volume corresponding with 1000 lt/ha).

Determination of the weed control (by visual observation and/or determination of % fresh weight reduction of weeds) for different application rates allows to establish the $EC_{90}$ value, i.e. the amount (in g of active ingredient/ha) allowing a 90% control of the weed to be combatted.

Theoretically, the amount (in g/ha) of Dimethenamid to be employed to allow 90 % of weed control, would be twice the amount of S-Dimethenamid, in a situation like this where the (1R, aRS)-diastereomeric mixture is found to be essentially inactive as a herbicide and has no apparent antagonistic effect on the herbicidal activity of the active component (i.e. on S-Dimethenamid).

The test results however indicated that the amount of S-Dimethenamid to be employed to allow good weed control is substantially less than half the amount of Dimethenamid to be applied. This is particularly true in a crop locus where the major weeds to be combatted are Echinochloa crus-galli, Amaranthus retroflexus and/or Setaria viridis, as may be illustrated by the following $EC_{90}$ values:

|  | $EC_{90}$ (g a.i./ha) | | |
| --- | --- | --- | --- |
|  | S-Dimethenamid (A) | Dimethenamid (B) | Ratio (B/A) |
| Greenhouse Tests |  |  |  |
| Echinochloa crus-galli | 79 | 305 | 3.86 |
| Amaranthus retroflexus | 136 | 415 | 3.05 |
| Field Tests |  |  |  |
| Echinochloa crus-galli | 38.8 | 140.8 | 3.6 |
| Setaria viridis | 8.9 | 33.7 | 3.8 |

The invention therefore provides a method of combatting weeds in a crop locus which comprises applying to the crop locus a herbicidally effective amount of S-Dimethenamid.

In general the amount of S-Dimethenamid to be applied to allow satisfactory weed control will lie in the range of from 400 g to 650 g/ha.

Furthermore, the above discussed field tests indicate that the crop tolerance for S-Dimethenamid and Dimethenamid is comparable. This suggests that the margin between the dosage allowing good weed control and the maximum dosage tolerant for crops is widened.

This is particularly advantageous in situations where the crop tolerance is not as ideal as observed for corn, e.g. where the crop locus is soybean, sugarbeet or sunflower.

S-Dimethenamid may be and preferably is employed as herbicidal composition in association with herbicidally acceptable diluent(s). Suitable formulations contain 0.01 % to 99% by weight of active ingredient, from 0 to 20 % herbicidally acceptable surfactant and 1 to 99.99% solid or liquid diluent(s). Higher ratios of surfactant to active ingredient are sometimes desirable and are achieved by incorporation into the formulation or by tank mixing. Application form of composition generally contain between 0.01 and 25% by weight of active ingredient. Lower or higher levels of active ingredient can, of course, be present depending on the intended use of the compound. Concentrated forms of composition intended to be diluted before use generally contain between 2 and 90%, preferably between 10 and 80% by weight of active ingredient.

Useful formulations of S-Dimethenamid include dusts, granules, pellets, suspension concentrates, wettable powders, emulsifiable concentrates and the like. They are obtained by conventional manner, e.g. by mixing the compounds of the invention with the diluent(s). More specifically liquid compositions are obtained by mixing the ingredients, fine solid compositions by blending and, usually grinding, suspensions by wet milling and granules and pellets by impregnating or coating (performed) granular carriers with the active ingredient or by agglomeration techniques.

Alternatively, the compounds of the invention may be used in micro-encapsulated form.

S-Dimethenamid has also very favorable storage properties, i.e. even when formulated in highly concentrated liquid compositions, e.g. in a 90% emulsifiable concentrate, it forms a stable liquid formulation which does not form any solid precipitate. No crystals of the active ingredient are detected even after long storage periods at low temperatures.

Herbicidally acceptable additives may be employed in the herbicidal compositions to improve the performance of the active ingredient and to reduce foaming, caking and corrosion.

Surfactant as used herein means a herbicidally acceptable material which imparts emulsifiability, spreading, wetting, dispersibility or other surface-modifying properties. Examples of surfactants are sodium lignin sulphonate and lauryl sulphate.

Diluents as used herein mean a liquid or solid herbicidally acceptable material used to dilute a concentrated material to a usable or desirable strength. For dusts or granules it can be e.g. talc, kaolin or diatomaceous earth, for liquid concentrate forms, for example a hydrocarbon such as xylene or an alcohol such as isopropanol, and for liquid application forms, i.a. water or diesel oil.

The compositions of this invention can also comprise other compounds having biological activity, e.g. compounds having similar or complementary herbicidal activity or compounds having antidotal, fungicidal or insecticidal activity.

S-Dimethenamid can be obtained in a manner known per se, e.g. by O-methylation of (1S,aRS)-2-chloro-N-(2,4-dimethyl-3-thienyl)-N-(2-hydroxy-1-methylethyl)acetamide. Such O-methylation may be carried out in a manner known per se.

In a alternative route of synthesis S-Dimethenamid may be obtained by reacting 2,4-dimethyl-3-hydroxythiophene of formula II

with (2S)-1-methoxypropyl-2-amine of formula III

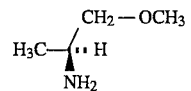

and reacting the obtained intermediate of formula IV

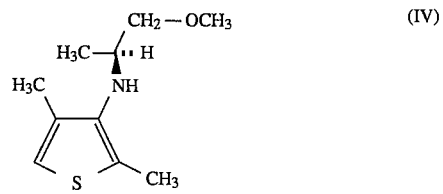

with chloroacetyl chloride.

In spite of the possible tautomerisation options of the intermediate IV, which would lead to loss of optical activity according to the following scheme 1:

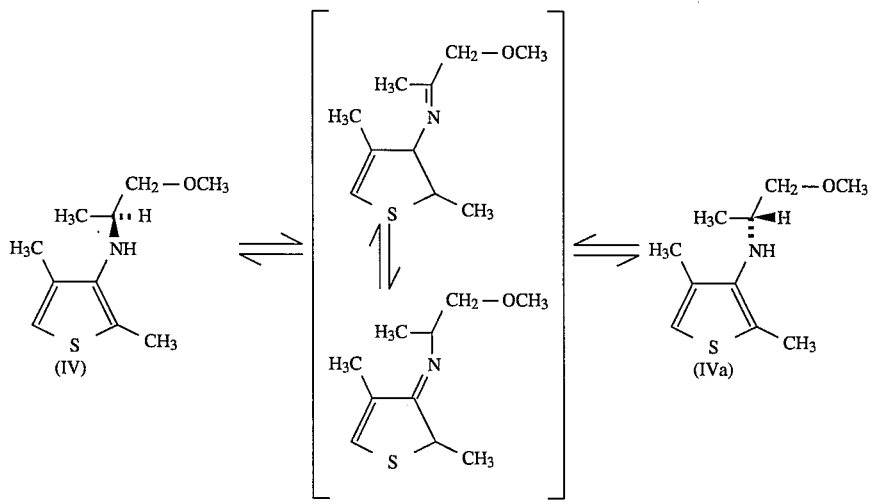

Surprisingly the coupling reaction (II+III–>IV) yields epimerically highly enriched material of formula IV in high optical purity (up to 95% ee) of the chiral carbon center with retention of the optical orientation. Of course, this reaction may also be used to prepare the 1R-isomer of the compound of formula I, if desired. In such case the reaction would be performed with the optical antipode of the compound of formula III as starting material, i.e. with (2R)-1-methoxypropyl-2-amine.

The coupling reaction (II+III –>IV) is conveniently carried out in an autoclave. In the coupling reaction the (2S)-methoxy-2-propylamine III may serve as solvent, or the reaction mixture can be diluted by organic solvents inert to the reaction conditions such as toluene. The reaction is advantageously carried out in the presence of an acid such as hydrochloric acid, acetic acid, or trifluoroacetic acid. The reaction temperature is suitably above +100° C., preferably between +150° C. and +220° C. The reaction pressure in the autoclave is preferably above 3 bar, e.g. between 6 bar and 10 bar.

The reaction of (1S,aRS)-N-(2,4-dimethyl-3-thienyl)-N-(2-methoxy-1-methylethyl)amine of formula IV with chloroacetylchloride (IV–>I) is carried out under conditions which are common in this type of amidation reaction, i.e.

preferably in the presence of a base and in the presence of an inert solvent. Analogous reaction conditions are known in the art, e.g. from EP-A-210 320.

The process II+III→IV→I as described above has been especially developed for the synthesis of the compound of formula I and thus is part of the present invention. Likewise the novel starting material of formula III and the novel intermediate of formula IV form additional parts of present invention.

The (2S)-1-methoxypropyl-2-amine of formula III may be prepared from methyl L-alanine by reduction with a suitable reducing agent, e.g. $NaBH_4$, to the (2S)-1-hydroxypropyl-2-amine and methylation of the hydroxy function, with a suitable methylating agent, e.g. dimethylsulfate.

Specific Examples of herbicidal compositions will now be described. Parts are by weight.

EXAMPLE A—Wettable Powder 26 parts S-Dimethenamid are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before used to a spray liquor with the desired concentration.

EXAMPLE B—Emulsion Concentrate

20 Parts of S-Dimethenamid, 40 parts of xylene, 30 parts of dimethyl formamide and 10 parts of emulsifier (e.g. ATLOX 4851 B, a Trade Mark for a blend of Ca-alkylarylsulphonate and a polyethoxylated triglyceride of Atlas Chemie GmbH) are thoroughly mixed until a homogeneous solution is obtained. The resulting emulsion concentrate is diluted with water before use.

EXAMPLE C—Granules 5 kg of S-Dimethenamid are dissolved in 25 methylene chloride. The solution is then added to 95 kg of granulated attapulgite (mesh size 24/48 mesh/inch) and thoroughly mixed. The solvent is then evaporated under reduced pressure.

EXAMPLE D—Emulsifiable Concentrate 80.1% by weight S-Dimethenamid 2.0% by weight emulsifier (e.g. ARMUL 33-manufactured by WITCO Chem. Corp.)

8.0% by weight emulsifier (e.g. ARMUL 88-manufactured by WITCO Chem. Corp.)

0.1% by weight antifoam agent (e.g. dimethylpolysiloxane)

9.8% by weight solvent (methyl oleate).

EXAMPLE E—Emulsifiable Concentrate

25% by weight S-Dimethenamid

10% by weight emulsifier mixture (e.g. ATLOX 4851 B)

65% by weight Xylene (technical).

The invention is further illustrated by the following Examples wherein temperatures are in °C., pressures are in Torr and Rf values are on silica gel, unless otherwise indicated.

EXAMPLE 1

(1S,aRS)-2-chloro-N-(2,4-dimethyl-3-thienyl)-N-(2-methoxy-1-methylethyl) acetamide To the well stirred, cooled (−10°) solution of 15.7 g (0.06 mol) of (1S,aRS)-2-chloro-N-(2,4-dimethyl-3-thienyl)-N-(2-hydroxy-1-methyl-ethyl)acetamide and 4.3 ml (0.03 ml) of boron trifluoride etherate in 350 ml of diethylether are added portionwise (six 50 ml portions) 300 ml of an ethereal solution of diazomethane-prepared from 32.2 g (0.15 mol) of N-methyl-N-nitroso-p-toluenesulfonamide according to the procedure described in Chem. Ind. 1990 708—taking care that the temperature does not rise above 0°. When the addition is complete, the ice/salt bath is removed and the reaction mixture is left to stir for a further 30 minutes at room temperature.

The organic layer is then separated and washed successively with 130 ml of 10 % $Na_2CO_3$-solution and 150 ml of water.

The brown oily residue left on rotevaporation of the dried ($Na_2SO_4$) solvent is chromatographed on a silica gel column.

Elution with hexane-diethyl ether 3:1 affords the reaction product as a pale yellow viscous liquid, which is homogeneous by TLC (Rf=0.5, silica gel, diethyl ether, visualised with a permanganate spray).

The $[\alpha]_D^{23}$-value ((+) 3.6°; c=1.072, $CH_3OH$) and the enantiomeric purity (98.4 %, by NMR analysis, using [Europium (III)-tris-(3-heptafluoropropyl-hydroxymethylene) d-camphorate] (also known and designated as Eu $(hfc)_3$) as the chiral shift reagent of the title compound), are determined on a sample, which has been distilled in a Kugelrohr apparatus at 150°/0.05 torr).

EXAMPLE 2

(1S,aRS)-2-chloro-N-(2,4-dimethyl-3-thienyl)-N-(2-methoxy-1-methylethyl) acetamide The solution of 11.0 g (0.042 mol) of (1S,aRS)-2-chloro-N-(2,4-dimethyl-3 -thienyl)-N-(2-hydroxy-1-methylethyl)acetamide, 10 ml (8.5 g, 0.082 mol) of 2,2-dimethoxypropane and 1.22 g (0.006 mol) of p-toluenesulphonic acid monohydrate in 65 ml of methanol is heated under reflux for 24 hours and then evaporated in vacuo. The residue is taken up in 300 ml of ethyl acetate, washed with 10% $NaHCO_3$-solution (70 ml) followed by water (70 ml) and the dried ($Na_2SO_4$,) solvent then removed with a rotary evaporator at aspiratory pressure. The residual yellow oil is chromatographed on a silica gel column. Elution with hexane-diethyl ether 2:1 affords the title compound as a faintly yellow viscous liquid, which is homogeneous by TLC (Rf=0.5, silica gel, diethyl ether, visualised with a permanganate spray).

The optical rotation $[\alpha]_D^{23}$-value=((+) 3.5°; c=1.102, $CH_3OH$) is determined on a sample, which has been double distilled in a Kugelrohr apparatus at 124°/0.01 torr.

EXAMPLE 3

(R)-2-[(4-Nitrophenyl)sulphonyloxy]propanoic acid isobutyl ester

To the well stirred solution of 25 ml (0.166 mol) of isobutyl(R)-lactate and 33.2 g (0.15 mol) of 4-nitrobenzenesulphonyl chloride in 150 ml of dry ethyl acetate are added dropwise without cooling-over a period of 10 minutes-21.3 ml (0.15 mol) of triethylamine. When all the $N(C_2H_5)_3$ has been introduced, the resulting reaction mixture is heated at 60° for one hour.

Then it is allowed to cool to ambient and left to stir for an additional 18 hours at this temperature.

At the end of this period the precipitated triethylamine hydrochloride is filtered off with suction. The filtrate is transferred to a separatory funnel, washed successively with water (100 ml), 2N HCl (100 ml), water (100 ml) and finally with 200 ml of 10% NaHCO$_3$-solution. The waxy solid left on rotevaporation of the dried (Na$_2$SO$_4$) organic phase is triturated with hexane, yielding the title compound as soft, yellow crystals, having a m.p. of 40°–41°. $[\alpha]_D^{23}$=(+) 21.0° (c=1.264, CH$_2$Cl$_2$).

EXAMPLE 4

N-(2,4-dimethyl-3-thienyl)-2-alanine isobutyl ester

To the stirred boiling solution of 22.6 g (0.178 mol) of 2,4-dimethyl-3-thiophenamine in 75 ml of dry chlorobenzene are added dropwise—under a dry nitrogen atmosphere- 32.1 g (0.09 mol) of (R)-2-[(4-ni-trophenyl)sulphonyloxy] propanoic acid isobutyl ester in 40 ml of dry chlorobenzene.

When the addition is complete, the resulting brown reaction mixture is boiled under reflux for 48 hours. Then it is allowed to cool to room temperature, the precipitated p-nitrobenzenesulphonate of the starting amine filtered off at the pump and washed with diethyl ether.

The brown oil left on rotevaporation of the combined filtrate and washings is dissolved in 200 ml of diethyl ether and-after decanting from a small portion of undissolved tar-washed with 0.1N HCl (100 ml) and water (100 ml).

The ethereal solution is dried (Na$_2$SO$_4$) and evaporated in vacuo.

The residual yellow oil, after chromatography on silica gel (elution with hexane-diethyl ether 4:1) is distilled under reduced pressure, to yield the title ester as a colourless liquid, b.p. 120°–125° C./0.4 Torr. $[\alpha]_D^{23}$=(−) 49.9° (c=1.117; CH$_2$Cl$_2$).

EXAMPLE 5

(S)-2-[(2,4-dimethyl-3-thienyl)amino]-1-propanol

To the well stirred, cooled (−5°) suspension of 2 g (0.0528 mol) of lithium aluminium hydride and 65 ml of dry tetrahydrofuran (THF) is added dropwise—under a dry nitrogen atmosphere—the solution of 6.8 g (0.0265 mol) of N-(2,4-dimethyl-3-thienyl)-L-alanine isobutyl ester in 65 ml of dry THF.

When the addition is complete, the ice/salt bath is removed and the reaction mixture left to stir for 20 hours at room temperature.

At the end of this period it is cooled in an ice bath and continuously treated with 15% aqueous NaOH-solution (3 ml) followed by water (3 ml).

The precipitate is filtered off with suction and washed with THF. The orange-coloured viscous liquid left on rotevaporation of the solvent is distilled in a Kugelrohr apparatus at 140°/0.4 Torr, to yield the title compound as a colourless oil: $[\alpha]_D^{23}$=(+) 5.6° (c=1.079, CH$_3$OH).

EXAMPLE 6

(1S,aRS)-2-chloro-N-(2,4-dimethyl-3-thienyl)-N-(2-hydroxy-1-methylethyl)-acetamide To the well stirred mixture of 34.3 g (0.186 mol) of (S)-2-[(2,4-dimethyl-3-thienyl) amino]-1-propanol, 26 g (0.186 mol) of K$_2$CO$_3$,91 ml of water and 370 ml of CH$_2$Cl$_2$ is added dropwise without cooling the solution of 15.5 ml (0.185 mol) of chloroacetyl chloride in 50 ml of CH$_2$Cl$_2$. After the exothermic reaction (35°) has subsided, stirring is continued for a further hour at ambient temperature. The methylene chloride layer is then separated, washed twice with water (200 ml) dried (Na$_2$SO$_4$) and evaporated in vacuo.

The residue is subjected to column chromatography on silica gel.

Elution with ethyl acetate-hexane 1:1 affords the title compound as a yellowish viscous oil, which solidifies completely to a crystalline mass, having a m.p. of 53°–54° : there is no change in the melting point after recrystallization from boiling diethyl ether (3.5 ml/g). $[\alpha]_D^{23}$=(+) 10.6 (c=1.047, CH$_3$OH).

Example 7

(1S,aRS)-2-chloro-N-(2,4-dimethyl-3-thienyl)-N-(2-methoxy-1-methylethyl)-acetamide a) (1S,aRS)-N-(2,4-dimethyl-3-thienyl)-N-(2-methoxy-1-methylethyl)-amine All operations were carried out under nitrogen. 8.33 g (65 mmol) of 2,4-dimethyl-3-hydroxythiophene are placed in a 200 ml round bottom flask and cooled with an ice bath. 15.1 g (170 mmol) (2S)-methoxy-propyl-2-amine (ee>96%) and subsequently 6.6 g (65 mmol) OF concentrated hydrochloric acid are added dropwise. After 10 min. the mixture is placed in an autoclave and heated to +200° C. for 3 hours (pressure 6 bar). After cooling, the mixture is distilled. Fractions boiling between +112° and 123° C./30 mbar are collected and diluted with diethylether. The combined organic phases are washed with diluted sodiumhydroxide solution. Usual workup procedures gives 4.0 g of (1S,aRS)-N-(2,4-dimethyl-3-thienyl)-N-(2-methoxy-1-methylethyl)-amine in the form of a yellow oil. The optical purity was determined by $^1$H-NMR shift experiments (Eu(tfc)$_3$, CDCl$_3$) to be ee=85% ±7%.

b) 0.5 g of (1S,aRS)-N-(2,4-dimethyl-3-thienyl)-N-(2-methoxy-1-methylethyl)-amine are dissolved in 5 ml dichloromethane and treated with 1.1 equivalents of triethylamine and 1 equivalent of chloroacetylchloride. Usual workup procedures by partition between water and dichloromethane gives (1S,aRS)-2-chloro-N-(2,4-dimethyl-3 -thienyl)-N-methoxy-1-methylethyl-acetamide as an oil which is distilled at 120° C./0.01 mm Hg to give (aRS, 1S)-Ia of $[\alpha]^{25}_D$=+2.9° (c=1, methanol). This corresponds to an ee=82%. (The optical rotation of the product of this example was compared to material prepared independently from the optical pure starting material isobutyl (R)-lactate as obtained from example 1, as well as $^1$H-NMR shift experiments using a chiral, non racemic EU-complex.)

Microanalysis (C$_{12}$H$_{18}$ClNO$_2$S)=275.734): calc. C 52.26% H 06.58% N 05.08% found C 52.3 H 06.3 N 05.0

Example 8

(2S)-1-methoxy-propyl-2-amine a) (2S)-1-hydroxypropyl-2-amine A 10 l reaction vessel is charged with 570 ml water, 1500 ml ethanol and then 444 g sodium borohydride. To this solution 418 g (3 mol) of methyl L-alanine hydrochloride in 570 ml water and 750 ml ethanol is added dropwise. The reaction temperature is kept between +50° and +55° C. After complete addition the reaction mixture is refluxed until no more hydrogen gas evolves. The still hot mixture is decanted and filtered. Most of the alcohol is evaporated whilst paying attention that the product is not distilled off as azeotrope. The remaining semi-solid material is heated 3 times with 2 l of ethanol, decanted and partially evaporated. The remaining water/ethanol solution is treated with gaseous hydrochloric acid until a pH value between 1 and 2 is reached and then evaporated, yielding a slight yellow oil. This oil is supended in dichloromethane, treated with 207 g of potassium carbonate and heated in a Dean-Stark trap to remove water. The mixture is filtered, washed with some dichloromethane and the solvents evaporated under normal pressure to yield (2S)-1-hydroxypropyl-2-amine as a yellow oil (147 g, water content below 1.6%) of $[\alpha]^{25}_D=+21.1°$ (c=6, ethanol).

b) A round bottom flask was charged with 25 g (2S)-1-hydroxypropyl-2-amine and 100 ml of dry ether. To this suspension 10 g of sodiumhydride (80% suspension in oil) is added in portions of 0.5 g with cooling. After the addition a solution of 40 g dimethylsulfate in 70 ml ether is added dropwise at a temperature below 20° C. After stirring for an additional 1 hour, the precipitated white solid is filtered off and washed with 100 ml ether. The filtrate is treated with 10 ml of diluted sodium hydroxide solution and stirred for 10 min. A solution of 30 ml of concentrated hydrochloric acid in 20 ml water is slowly added to the stirred solution. Evaporation of the solvents give 44 g crude (2S)-1-methoxy-propyl-2-amine as the hydrochloride salt which is suspended in dichloromethane and treated with 60 g potassium carbonate. This suspension is refluxed in a Dean Stark trap. Evaporation of the solvent at normal pressure and subsequent distillation at +95° C. gives (2S)-1-methoxy-propyl-2-amine as an oil of 80% chemical purity and ee>95%. This material may be further purified by distillation through a spinning band column.

The optical purity may be checked by GC analysis as follows: 5 mg of the amine are dissolved in 2 ml of dichloromethane and treated with 100 mg of pentafluoropropanoic acid anhydride. After the solution is cooled to +25° C., 1 µl is analyzed on an octakis-(2,6-di-O-pentyl-3-O-butyryl-γ-cyclodextrin column.

What we claim is:

1. (1S,aRS)-2-chloro-N-(2,4-dimethyl-3-thienyl)-N-(2-methoxy-1-methylethyl)acetamide.

2. A herbicidal composition comprising an herbicidally effective amount of the compound of claim 1.

3. A method of combatting weeds which comprises applying to the weeds or the weed locus, a herbicidally effective amount of the compound of claim 1.

4. A method of combatting weeds in a crop locus which comprises applying to the crop locus a herbicidally effective amount of the compound of claim 1.

5. The method of claim 4 wherein the crop is corn, soybean, sugarbeet or sunflower.

6. The method of claim 5 whereby the compound is applied post-sowing and pre-emergence of the crop.

7. A process for preparing (1S,aRS)-2-chloro-N-(2,4-dimethyl-3-thienyl)-N-(2-methoxy-1-methylethyl)acetamide according to claim 1, characterized by reacting 2,4-dimethyl-3-hydroxythiophene of formula II

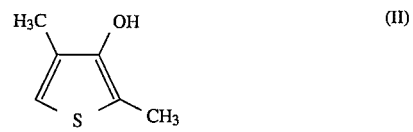

with (2S)-1-methoxypropyl-2-amine of formula III

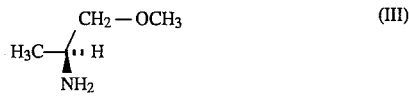

and reacting the obtained intermediate of formula IV

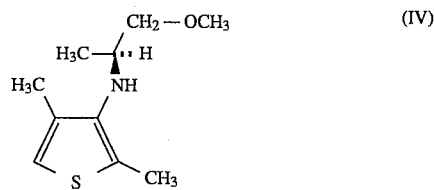

with chloroacetylchloride.

8. (1S,aRS)-N-(2,4-dimethyl-3-thienyl)-N-(2-methoxy-1-methylethyl)-amine.

* * * * *